(12) United States Patent
Lang et al.

(10) Patent No.: US 8,106,204 B2
(45) Date of Patent: Jan. 31, 2012

(54) SUBSTITUTED 2-AMINO-4-PHENYLDIHYDROQUINOLINES, PROCESSES FOR THEIR PREPARATION, PHARMACEUTICAL COMPOSITIONS AND METHODS FOR THEIR USE

(75) Inventors: Hans-Jochen Lang, Frankfurt am Main (DE); John Weston, Frankfurt am Main (DE); Uwe Heinelt, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 583 days.

(21) Appl. No.: 12/212,294

(22) Filed: Sep. 17, 2008

(65) Prior Publication Data

US 2009/0118329 A1 May 7, 2009

Related U.S. Application Data

(63) Continuation of application No. PCT/EP2007/001983, filed on Mar. 8, 2007.

(30) Foreign Application Priority Data

Mar. 18, 2006 (DE) .......................... 10 2006 012545

(51) Int. Cl.
*C07D 215/04* (2006.01)
(52) U.S. Cl. ...................................... 546/159
(58) Field of Classification Search ............... 546/159
See application file for complete search history.

(56) References Cited

U.S. PATENT DOCUMENTS 3,538,101 A 11/1970 Carney, et al.

FOREIGN PATENT DOCUMENTS

WO WO 03/048129 6/2003

OTHER PUBLICATIONS

Delcros, J Med Chem. vol. 49 No. 1, pp. 232-245, 2006.*

* cited by examiner

*Primary Examiner* — D M Seaman
(74) *Attorney, Agent, or Firm* — Scully, Scott, Myrphy & Presser, P.C.

(57) ABSTRACT

The invention relates to NHE-3 inhibitor compounds of formula I:

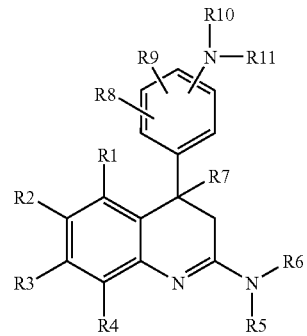

In which R1-R11 are more specifically defined herein. These substituted 2-amino-4-phenyl-dihydroquinolines are useful the treatment of various renal and respiratory disorders such as acute or chronic renal failure, for impairments of biliary function and respiratory impairments such as snoring, sleep apneas or stroke. Formulations comprising them and methods for their use are also described herein.

10 Claims, No Drawings

SUBSTITUTED 2-AMINO-4-PHENYLDIHYDROQUINOLINES, PROCESSES FOR THEIR PREPARATION, PHARMACEUTICAL COMPOSITIONS AND METHODS FOR THEIR USE

CROSS REFERENCE TO RELATED APPLICATIONS

This application is a continuation of PCT/EP2007/001983 filed on Mar. 8, 2007 which is incorporated herein by reference in its entirety; which claims the benefit of German patent application No. 10 2006 012 545.2 filed on Mar. 18, 2006.

FIELD OF THE INVENTION

The present invention relates generally to pharmaceutical compounds and compositions comprising them for the treatment of various renal and respiratory disorders such as acute or chronic renal failure, for impairments of biliary function and respiratory impairments such as snoring, sleep apneas or stroke. More specifically, the present invention relates to compounds of the type of substituted 2-amino-4-phenyl-dihydroquinolines, formulations comprising them and methods for their use.

BACKGROUND OF THE INVENTION

The invention relates generally to novel substituted 2-amino-4-phenyl-dihydroquinolines compounds and compositions comprising them. Pharmaceutical compositions comprising compounds of this type are useful in the prevention or treatment of various disorders. Thus, the compounds can be employed inter alia for renal disorders such as acute or chronic renal failure, for impairments of biliary function, for respiratory impairments such as snoring or sleep apneas or for stroke.

The compounds according to the invention are effective inhibitors of the cellular sodium-proton transporter (Na/H exchanger) which is elevated in numerous disorders (essential hypertension, atherosclerosis, diabetes, etc.), also in those cells which are readily amenable to measurements, such as, for example, in erythrocytes, platelets or leukocytes. The compounds used according to the invention are therefore suitable as excellent and simple scientific tools, for example in their use as diagnostic aids for determining and distinguishing different types of hypertension, but also of atherosclerosis, of diabetes and late complications of diabetes, proliferative disorders etc.

The compounds of the formula I are moreover suitable for preventive therapy to prevent the development and for the treatment of high blood pressure, for example of essential hypertension, because they reduce or completely inhibit the re-absorption of NaCl in the tubular system of the kidneys. Accordingly, they are also outstandingly suitable as combination and formulation partners for drugs used for treating high blood pressure. Examples of possible combinations are diuretics having a thiazide-like action, loop diuretics, aldosterone and pseudo-aldosterone antagonists, such as hydrochlorothiazide, indapamide, polythiazide, furosemide, piretanide, torasemide, bumetanide, amiloride, triamterene. The NHE inhibitors of the present invention can further be used in combination with ACE inhibitors such as, for example, ramipril, enalapril or captopril. Further beneficial combination partners are also β-blockers.

The described NHE inhibitors can likewise be used in the prevention and for the treatment of thrombotic disorders because, as NHE inhibitors, they are able to inhibit both platelet aggregation itself and, in addition, able to inhibit or prevent the excessive release of coagulation mediators, in particular of von Willebrand factor. The NHE inhibitors of the present invention can therefore be combined with further anticoagulant active ingredients such as, for example, acetylsalicylic acid, thrombin antagonists, factor Xa antagonists, drugs with fibrinolytic activity, factor VIIa antagonists etc. Combined use of the present NHE inhibitors with NCBE inhibitors is particularly beneficial.

It has additionally been found that NHE inhibitors show a beneficial effect on serum lipoproteins. It is generally acknowledged that blood lipid levels which are too high, so-called hyper-lipoproteinemias, represent a considerable risk factor for the development of arteriosclerotic vascular lesions, especially coronary heart disease. The reduction of elevated serum lipoproteins therefore has exceptional importance for the prophylaxis and regression of atherosclerotic lesions. The compounds used according to the invention can therefore be used for the prophylaxis and regression of atherosclerotic lesions by eliminating a causal risk factor. The NHE inhibitors of the invention can also be combined in a beneficial manner with other anti-arteriosclerotic active ingredients such as a substance from the class of fibrates, an upregulator of LD2 receptor activity such as MD-700 and LY295427 or a cholesterol or bile acid absorption inhibitor or an anti-hyper-cholesterolemic agent from the class of statins, such as, for example, pravastatin, lovastatin, simvastatin.

With this protection of the vessels against the syndrome of endothelial dysfunction, compounds of the formula I are valuable drugs for the prevention and treatment of coronary vasospasms, peripheral vascular diseases such as intermittent claudication, of atherogenesis and of atherosclerosis, of left-ventricular hypertrophy and of dilated cardiomyopathy, and thrombotic disorders.

It has been possible to show that compounds of the formula I represent excellent inhibitors of the sodium-hydrogen exchanger (NHE), especially of the sodium-hydrogen exchanger of subtype 3 (NHE-3).

NHE-3 inhibitors disclosed to date are derived for example from compounds of the acylguanidine type (EP825178), norbornylamine type (WO0144164), 2-guanidino-quinazoline type (WO0179186) or benzamidine type (WO0121582, WO0172742). Squalamine, which is likewise described as an NHE-3 inhibitor (M. Donowitz et al. Am. J. Physiol. 276 (Cell Physiol. 45): C136-C144), does not according to current knowledge act directly like the compounds of formula I, but acts via an indirect mechanism and thus reaches its maximum strength of effect after only one hour.

Tetrahydroisoquinolines as inhibitors of the sodium-hydrogen exchanger of subtype 3 (NHE-3) are described for example in the patent applications WO03048129, WO2004085404 and the German applications 102004046492.8 and 102005001411.9. The related compound class of tetrahydroisoquinolinium salts is described as NHE-3 inhibitors in the patent application WO03055880.

It has now surprisingly been found that the compounds of the formula I described herein likewise represent potent inhibitors of NHE-3 and moreover have advantageous pharmacological and pharmacokinetic properties.

NHE-3 is found in the body of various species preferentially in the bile, the intestine and the kidney (Larry Fliegel et al, Biochem. Cell. Biol. 76: 735-741, 1998), but has also been detectable in the brain (E. Ma et al. Neuroscience 79: 591-603).

Because of their NHE-inhibitory properties, the compounds of the formula I are suitable for the prevention and treatment of diseases which are caused by activation of or by an activated NHE, and of diseases which are caused secondarily by the NHE-related damage.

The compounds of the formula I can also be employed for the treatment and prevention of diseases where NHE is only partially inhibited, for example by use of a lower dosage.

The use of the compounds of the invention relates to the prevention and treatment of acute and chronic diseases in veterinary and human medicine.

As a consequence of their pharmacological effects, the compounds of the formula I are particularly suitable for leading to an improvement in respiratory drive. They can therefore be used for the treatment of impaired respiratory conditions like those which may occur for example in the following clinical conditions and diseases: impaired central respiratory drive (e.g. central sleep apneas, sudden infant death, postoperative hypoxia), muscle-related respiratory impairments, respiratory impairments following long-term ventilation, respiratory impairments associated with adaptation to high altitude, obstructive and mixed form of sleep apneas, acute and chronic pulmonary diseases with hypoxia and hypercapnia. In addition, the compounds increase the tone of the muscles of the upper airways, so that snoring is suppressed. Said compounds are therefore advantageously used for the manufacture of a medicament for the prevention and treatment of sleep apneas and muscle-related respiratory impairments and for the manufacture of a medicament for the prevention and treatment of snoring.

SUMMARY OF THE INVENTION

The invention relates to NHE-3 inhibitor compounds of formula I:

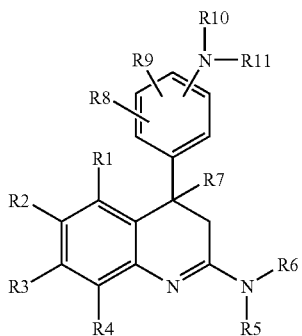

In which R1-R11 are more specifically defined herein. These substituted 2-amino-4-phenyl-dihydroquinolines are useful the treatment of various renal and respiratory disorders such as acute or chronic renal failure, for impairments of biliary function and respiratory impairments such as snoring, sleep apneas or stroke. Formulations comprising them and methods for their use are also described herein.

DETAILED DESCRIPTION OF THE INVENTION

The invention relates to novel substituted 2-amino-4-phenyl-dihydroquinolines NHE-3 inhibitor compounds which are useful the treatment of various renal and respiratory disorders. Said compounds comprise the structure of formula I:

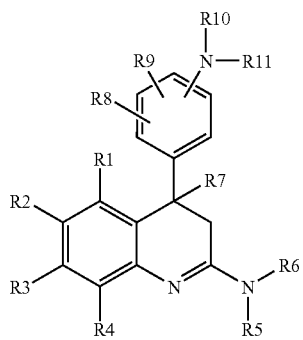

in which R1, R2, R3 and R4 are independently selected from the group consisting of hydrogen, F, Cl, Br, I, CN, $NO_2$, $CF_3$, $CH_3$—$SO_2$, an alkyl with 1-4 carbon atoms, $NH_2$, NH—$CH_3$ and $N(CH_3)_2$;

R5 and R6 are independently selected from the group consisting of hydrogen, a C1-C6 alkyl having 1-6 carbon (C) atoms, $CF_3$—$CH_2$—, cycloalkyl having 3, 4, 5 or 6 C atoms or cyclopropyl-$CH_2$—, or R5 and R6 together with the nitrogen atom to which they are bonded, form a 4-, 5-, 6-, 7-, 8-, 9- or 10-membered ring in which one or two $CH_2$ groups may be replaced independently of one another by NR12, sulfur, oxygen, C(O) or $SO_2$; and wherein R12 is hydrogen, alkyl having 1, 2, 3 or 4 C atoms or cycloalkyl having 3, 4, 5 or 6 C atoms;

R7 is hydrogen or alkyl having 1, 2, 3 or 4 C atoms;

R8 and R9 are independently selected from the group consisting of hydrogen, F, Cl, Br, OH, an alkyl having 1, 2, 3 or 4 C atoms, $CH_3O$, $CF_3$, or $CH_3SO_2$;

R10 and R11 are R13-$(C_mH_{2m})$—$B_n$, wherein
m is zero, 1, 2, 3 or 4;
n is zero or 1, and;
B is —CO—, —CONR14- or —$SO_2$—; wherein R14 is hydrogen or alkyl having 1, 2, 3, 4, 5 or 6 C atoms;
R13 is independently selected from the group consisting of hydrogen, alkyl having 1, 2, 3 or 4 C atoms, cycloalkyl having 3, 4, 5 or 6 C atoms, 1-pyrrolidinyl, 1-piperidinyl, 1-(4-methylpiperazinyl), 1-morpholinyl, —COOR15, OR16, NR17R18 or phenyl which has independently of one another 1 or 2 substituents selected from the group of chlorine, fluorine, methyl and methoxy;
R15, R16, R17 and R18 are independently selected from the group consisting of independently of one another hydrogen or alkyl having 1, 2, 3, 4, 5 or 6 C atoms;
or
R10 and R11 together with the nitrogen atom to which they are bonded, form a 4-, 5-, 6-, 7-, 8-, 9- or 10-membered ring in which one, two or three $CH_2$ groups may be replaced independently of one another by NR19, sulfur, oxygen, C(O) or $SO_2$;
wherein R19 is hydrogen, alkyl having 1, 2, 3 or 4 C atoms or cycloalkyl having 3, 4, 5 or 6 C atoms and the pharmaceutically acceptable salts and trifluoroacetates thereof.

Preferably, the present invention comprises compounds of the formula I in which R1, R2, R3 and R4 are independently selected from the group consisting of hydrogen, F, Cl, Br, CN, $CF_3$, $CH_3$—$SO_2$, alkyl having 1, 2, 3 or 4 C atoms, $NH_2$, NH—$CH_3$ and $N(CH_3)_2$;

R5 and R6 are independently selected from the group consisting of hydrogen, an alkyl having 1, 2, 3, 4, 5 or 6 C atoms, $CF_3$—$CH_2$—, a cycloalkyl having 3, 4, 5 or 6 C atoms or cyclopropyl-$CH_2$—,
or,
R5 and R6 form together with the nitrogen atom to which they are bonded a 4-, 5-, 6-, 7-, 8-, 9- or 10-membered ring;
R7 hydrogen;
R8 and R9 are independently selected from the group consisting of hydrogen, F, Cl, OH, alkyl having 1, 2, 3 or 4 C atoms, $CH_3O$, $CF_3$, or $CH_3SO_2$;
R10 and 11 are R13-$(C_mH_{2m})$—$B_n$, where
m is zero, 1, 2, 3 or 4;
n is zero or 1;
B is —CO—, —CONR14- or —$SO_2$—; wherein
R14 is hydrogen or alkyl having 1, 2, 3, 4, 5 or 6 C atoms;
R13 is selected from the group consisting of hydrogen, alkyl having 1, 2, 3 or 4 C atoms, cycloalkyl having 3, 4, 5 or 6 C atoms, 1-pyrrolidinyl, 1-piperidinyl, 1-(4-methylpiperazinyl), 1-morpholinyl, —COOR15, OR16, NR17R18 or phenyl which has independently of one another 1 or 2 substituents selected from the group of chlorine, fluorine, methyl and methoxy and wherein R15, R16, R17 and R18 are independently of one another hydrogen or alkyl having 1, 2, 3, 4, 5 or 6 C atoms;
or
R10 and R11 together with the nitrogen atom to which they are bonded, form a 4-, 5-, 6-, 7-, 8-, 9- or 10-membered ring in which one $CH_2$ group may be replaced by oxygen or NR19, and R19 hydrogen or alkyl having 1, 2, 3 or 4 C atoms; and the pharmaceutically acceptable salts and trifluoroacetates thereof.

More preferably, the present invention comprises compounds of formula I in which
R1, R2, R3 and R4 form
independently of one another hydrogen, F, Cl, Br, CN, $CF_3$, $CH_3$—$SO_2$, methyl, ethyl, $NH_2$, NH—$CH_3$ or N($CH_3$)$_2$;
R5 and R6 are independently are independently selected from the group consisting of hydrogen, methyl, ethyl, isopropyl, $CF_3$—$CH_2$ or a cycloalkyl having 3, 4, 5 or 6 C atoms;
R7 is hydrogen;
R8 and R9 are independently selected from the group consisting of hydrogen, Cl or methyl;
R10 and 11 are independently selected from the group consisting of R13-$(C_mH_{2m})$—$B_n$, wherein
m zero, 1, 2, 3 or 4;
n zero or 1;
B —CO—, —CONR14- or —$SO_2$— and R14 is a hydrogen or alkyl having 1, 2, 3, 4, 5 or 6 C atoms;
R13 hydrogen, methyl, cycloalkyl having 3, 4, 5 or 6 C atoms, 1-pyrrolidinyl, 1-piperidinyl, 1-(4-methylpiperazinyl), —COOR15, OR16 or NR17R18;
R15, R16, R17 and R18 are independently selected from the group consisting of hydrogen or alkyl having 1, 2, 3, 4, 5 or 6 C atoms;
or
R10 and R11 together with the nitrogen atom to which they are bonded form a 4-, 5-, 6-, 7-, 8-, 9- or 10-membered ring, in which one $CH_2$ group may be replaced by oxygen or NR19 which is hydrogen or methyl;
and the pharmaceutically acceptable salts and trifluoroacetates thereof.

Even more preferably, compounds of the present invention comprise compounds of formula I in which:
R1 and R3 R2 and R4 are independently selected from the group consisting of independently of one another hydrogen or Cl;
R5 and R6 independently are independently selected from the group consisting of hydrogen, methyl or ethyl;
R7 is hydrogen;
R8 and R9 are independently selected from the group consisting of hydrogen or Cl;
R10 and 11 are independently selected from the group consisting of R13-$(C_mH_{2m})$—$B_n$, wherein
m is zero, 1, 2, 3 or 4;
n is zero or 1;
B is —CONR14- wherein R14 is hydrogen or methyl;
R13 is selected from the group consisting of hydrogen, methyl, cycloalkyl having 3, 4, 5 or 6 C atoms, 1-pyrrolidinyl, 1-piperidinyl, 1-(4-methylpiperazinyl), —COOR15, OR16 or NR17R18;
R15, R16, R17 and R18 are hydrogen or alkyl having 1, 2, 3, 4, 5 or 6 C atoms;
or
R10 and R11 together with the nitrogen atom to which they are bonded form a 4-, 5-, 6-, 7-, 8-, 9- or 10-membered ring in which one $CH_2$ group may be replaced by NR19;
and R19 is hydrogen or methyl;
and the pharmaceutically acceptable salts and trifluoroacetates thereof.

Even more preferably are those compounds of formula I in which
R1 and R3 are hydrogen;
R2 and R4 are hydrogen or Cl;
R5 and R6 are hydrogen, methyl or ethyl;
R7 is hydrogen;
R8 and R9 are independently of one another hydrogen or Cl;
R10 and 11 independently of one another R13-$(C_mH_{2m})$—$B_n$, where
m zero, 1, 2, 3 or 4;
n zero or 1;
B —CONR14- and R14 is hydrogen or methyl;
R13 is hydrogen, methyl, or NR17R18 wherein;
R17 and R18 are hydrogen, methyl or ethyl, and;
and the pharmaceutically acceptable salts and trifluoroacetates thereof.

Most preferably, the present invention comprises compounds of formula I selected from the group consisting of:
2-amino-4-(4-aminophenyl)-6-chloro-3,4-dihydroquinoline,
4-(4-aminophenyl)-6-chloro-2-ethylamino-3,4-dihydroquinoline,
4-(4-aminophenyl)-6-chloro-2-diethylamino-3,4-dihydroquinoline, and
N-(2-dimethylaminoethyl)-N'-4-[(6-chloro-3,4-dihydro-2-diethylaminoquinolin-4-yl)phenyl]urea,
and the pharmaceutically acceptable salts and trifluoroacetates thereof.

In one embodiment, the most preferred compounds of formula I are those in which the substituents R1, R2, R3 and R4 are selected from the group consisting of hydrogen, F, Cl, Br, CN, $CF_3$, $CH_3$—$SO_2$ and alkyl having 1, 2, 3 or 4 C atoms, for example methyl or ethyl, $NH_2$, NH—$CH_3$ or N($CH_3$)$_2$; particularly preferred compounds of formula I are those in which R1 and R3 are hydrogen and R2 and R4 are independently selected from the group consisting of hydrogen, F, Cl, Br, CN, $CF_3$, $CH_3$—$SO_2$, methyl, ethyl, $NH_2$, NH—$CH_3$ or N($CH_3$)$_2$, for example hydrogen or Cl; in a further embodiment, preferred compounds of the formula I are those in which R1, R3 and R4 are hydrogen, and R2 is F, Cl, Br, CN, $CF_3$, $CH_3$—$SO_2$, methyl, ethyl, $NH_2$, NH—$CH_3$ or N($CH_3$)$_2$, for example Cl.

In another embodiment, preferred compounds of the formula I are those in which R5 and R6 are hydrogen, alkyl having 1, 2, 3, 4, 5 or 6 C atoms, $CF_3$—$CH_2$— or cycloalkyl having 3, 4, 5 or 6 C atoms, or R5 and R6 form together with the nitrogen atom to which they are bonded a 4-, 5-, 6-, 7-, 8-, 9- or 10-membered ring; in a further embodiment, preferred compounds of the formula I are those in which R5 and R6 are independently of one another hydrogen, methyl, ethyl, isopropyl, $CF_3$—$CH_2$ or cycloalkyl having 3, 4, 5 or 6 C atoms, in particular hydrogen, methyl or ethyl, for example hydrogen or ethyl.

In a further embodiment, preferred compounds of the formula I are those in which R7 is hydrogen or methyl, In yet another embodiment, preferred compounds of formula I are those in which the radicals R8 and R9 are described independently of one another by hydrogen, F, Cl, OH, alkyl having 1, 2, 3 or 4 C atoms, $CH_3O$, $CF_3$, or $CH_3SO_2$; particularly preferred compounds of the formula I are those in which R8 and R9 are described independently of one another by hydrogen, Cl or methyl, in particular hydrogen or Cl, for example hydrogen.

The radical NR10R11 on the phenyl ring may be bonded in the ortho, meta or para position to the dihydroisoquinoline group, In one embodiment, preferred compounds of the formula I are those in which the radicals R10 and R11 are described independently of one another by R13-$(C_mH_{2m})$—$B_n$ or R10 and R11 form together with the nitrogen atom to which they are bonded a 4-, 5-, 6-, 7-, 8-, 9- or 10-membered ring in which one $CH_2$ group may be replaced by oxygen or NR19, where R19 is hydrogen or alkyl having 1, 2, 3 or 4 C atoms, in particular hydrogen or methyl; in a further embodiment, preferred compounds of the formula I are those in which the radicals R10 and R11 are described independently of one another by R13-$(C_mH_{2m})$—$B_n$.

In another embodiment, preferred compounds of the formula I are those in which m is zero, 1 or 2, for example zero or 2.

In one embodiment, preferred compounds of the formula I are those in which n is zero; in a further embodiment, preferred compounds of the formula I are those in which n is 1.

In one embodiment, preferred compounds of the formula I are those in which B is —CONR14-, where R14 is hydrogen or alkyl having 1, 2, 3, 4, 5 or 6 C atoms, in particular hydrogen or methyl, for example hydrogen.

In one embodiment, preferred compounds of the formula I are those in which R13 is described by hydrogen, methyl, ethyl, isopropyl, cycloalkyl having 3, 4, 5 or 6 C atoms, 1-pyrrolidinyl, 1-piperidinyl, 1-(4-methylpiperazinyl), —COOR15, OR16 or NR17R18, where R15, R16, R17 and R18 are independently of one another hydrogen or alkyl having 1, 2, 3, 4, 5 or 6 C atoms; in a further embodiment, preferred compounds of the formula I are those in which R13 is described by hydrogen, methyl or NR17R18, where R17 and R18 independently of one another are hydrogen or alkyl having 1, 2, 3, 4, 5 or 6 C atoms, in particular hydrogen, methyl or ethyl, for example methyl; particularly preferred compounds of the formula I are those in which R13 is hydrogen or dimethylamino.

If the compounds of the formula I comprise one or more centers of asymmetry, these may independently of one another have either the S or the R configuration. The compounds may be in the form of optical isomers, of diastereomers, of racemates or of mixtures in all ratios thereof. The compounds of the formula I may moreover be in the form of rotational isomers.

The present invention includes all possible tautomeric forms of the compounds of the formulae I.

The present invention further includes derivatives of the compounds of the formula I, for example solvates such as hydrates and alcohol adducts, esters, prodrugs and other physiologically acceptable derivatives of the compounds of the formula I, and active metabolites of the compounds of the formula I. The invention likewise includes all crystal modifications of the compounds of the formula I.

Alkyl radicals may be straight-chain or branched. This also applies when they have substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl or hexyl. Preferred alkyl radicals are methyl, ethyl, n-propyl, isopropyl, n-butyl, tert-butyl, n-pentyl, n-hexyl.

Examples of cycloalkyl radicals are cyclopropyl, cyclobutyl, cyclopentyl, cyclohexyl, cycloheptyl or cyclo-octyl. One or more $CH_2$ groups in the cycloalkyl radicals may be replaced by O, NH or N-alkyl, for example $NCH_3$. This also applies to cycloalkylmethyl radicals.

Examples of NR5R6 rings are morpholine, pyrrolidine, piperidine, piperazine, N-methylpiperazine, pyrrolidin-2-one, pyrrolindine-2,5-dione, imidazolidine, 3-methyl-imidazolindine, imidazolidin-2-one, 3-methylimidazolidin-2-one, imidazolidine-2,4-dione and 1-methylimidazolidine-2,4-dione, especially pyrrolidine and piperidine, for example pyrrolidine.

Examples of NR10R11 rings are morpholine, pyrrolidine, piperidine, piperazine, N-methylpiperazine, pyrrolidin-2-one, pyrrolindine-2,5-dione, imidazolidine, 3-methyl-imidazolindine, imidazolidin-2-one, 3-methylimidazolidin-2-one, imidazolidine-2,4-dione and 1-methylimidazolidine-2,4-dione, especially pyrrolindine-2,5-dione and imidazolidine-2,4-dione, for example imidazolidine-2,4-dione.

The terminal $CH_3$ groups in an alkyl radical are also regarded as $CH_2$ units and, in this connection, are understood as $CH_2$—H groups.

If a variable, such as for example, cycloalkyl or R1, occurs more than once as component, the definitions of the variables are independent of one another at each occurrence.

If the compounds of the formula I comprise one or more acidic or basic groups or one or more basic heterocycles, the invention also includes the corresponding physiologically or toxicologically acceptable salts, in particular the pharmaceutically usable salts. Thus, the compounds of formula I may be de-protonated on an acidic group and be used for example as alkali metal salts, preferably sodium or potassium salts, or as ammonium salts, for example as salts with ammonia or organic amines or amino acids. Since compounds of the formula I always comprise at least one basic group, they can also be prepared in the form of their physiologically tolerated acid addition salts, e.g. with the following acids: from inorganic acids such as hydrochloric acid, sulfuric acid or phosphoric acid or from organic acids such as acetic acid, citric acid, tartaric acid, lactic acid, malonic acid, methanesulfonic acid, fumaric acid. Suitable acid addition salts in this connection are salts of all pharmacologically acceptable acids (this group also corresponds to the physiologically acceptable anions), for example halides, especially hydrochlorides, lactates, sulfates, citrates, tartrates, acetates, phosphates, methylsulfonates, p-toluenesulfonates, adipates, fumarates, gluconates, glutamates, glycerolphosphates, maleates and pamoates, but also trifluoroacetates.

The invention also relates to the process described below for preparing the compounds of the formula I.

The compounds of the formula I in which R10 and R11 are hydrogen and which are described herein can be prepared, for example, starting from the quinoline derivatives of the formula II by reduction to the corresponding 3,4-dihydroquinolines of the formula Ia

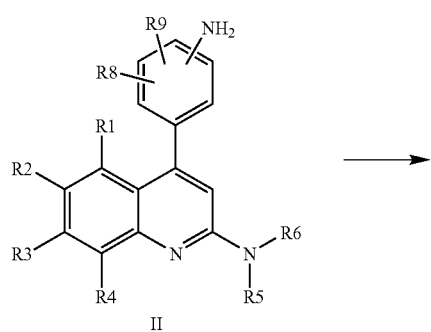

II

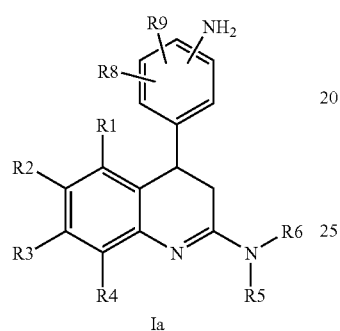

Ia wherein the substituents R1, R2, R3, R4, R5, R6, R8 and R9 are defined above. The reduction of quinoline derivatives of the formula II to the corresponding 3,4-dihydroquinolines of the formula Ia can be carried out, for example, using a sodium amalgam alloy such as that disclosed in U.S. Pat. No. 3,538,101 to Carney which is hereby incorporated by reference herein.

Further compounds of the invention of the formula I can be prepared from the compounds according to the invention of the formula I a) for example by derivatization of the amino group on the phenyl radical by processes known to the skilled worker. In these cases, for example, the amino group of the compounds 1a) is reacted with alkylating agents, acylating agents or sulfonating reagents of the formula R10-L and/or R11-L, advantageously in the presence of an auxiliary base, such as pyridine, triethylamine or Hünig's base, in a manner known to the skilled worker. It is likewise suitable to use isocyanates of the formulae R10-N=C=O and/or R11-N=C=O in a manner known to the skilled worker for preparing corresponding urea derivatives of the formula Ib or Ic

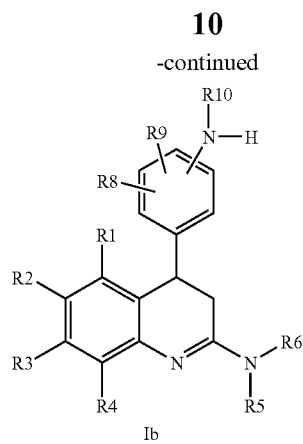

Ib

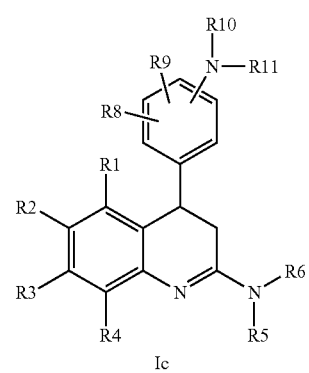

Ic where the substituents R1, R2, R3, R4, R5, R6, R8, R9, R10 and R11 have the meaning indicated above, but R10 and R11 are not hydrogen, and L is F, Cl, Br, I, —OR, —OC(O)R or —SR, where R is alkyl having 1, 2, 3, 4, 5 or 6 C atoms, for example methyl or ethyl, and L may be —SR when B is —C(O)—. It is also possible for carrying out the reactions stepwise for example for the monosubstituted compound of the invention of the formula Ib to be obtained and isolated and/or subsequently reacted to give the disubstituted compound of the formula Ic.

The compounds of the formula II can be converted analogously by derivatization of the amino group on the phenyl radical by processes known in the art into compounds of the formula IIIa or IIIb,

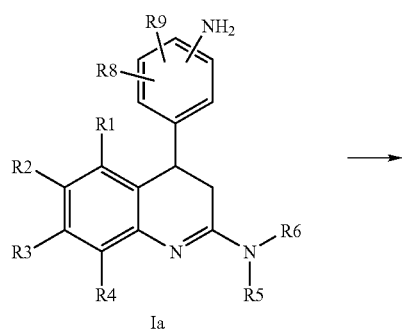

Ia

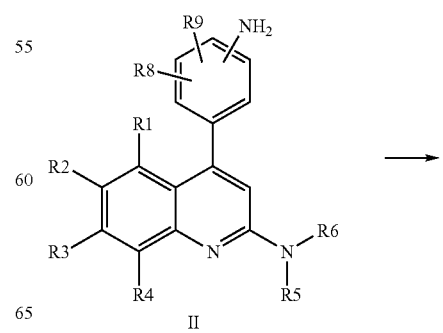

II

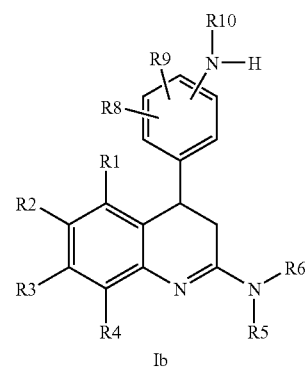

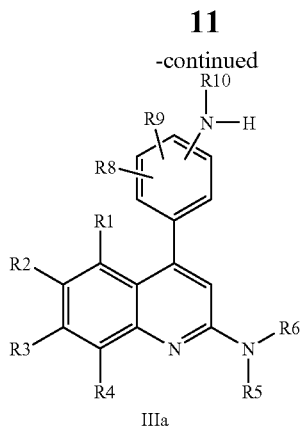

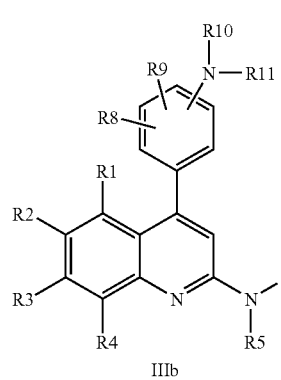

wherein the substituents R1, R2, R3, R4, R5, R6, R8, R9, R10 and R11 are as described above, with the further stipulation that R10 and R11 are not hydrogen.

The quinoline derivatives of formula IIIa or IIIb are obtained in this way wherein R10 and R11 are not hydrogen which can subsequently be reduced in a known manner, for example with sodium amalgam alloy, to the corresponding 3,4-dihydroquinoline derivatives of the invention of the formula Ib or Ic, where the substituents R1, R2, R3, R4, R5, R6, R8, R9, R10 and R11 are as defined above, with the further stipulation that R10 and R11 are not hydrogen.

The anilines of the formula II used above are preferably obtained by reducing the corresponding nitro compounds of the formula Iva:

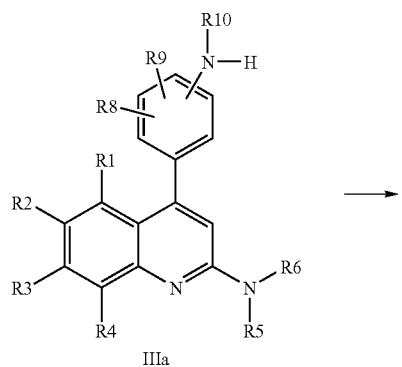

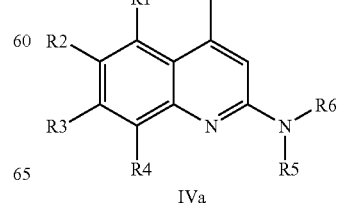

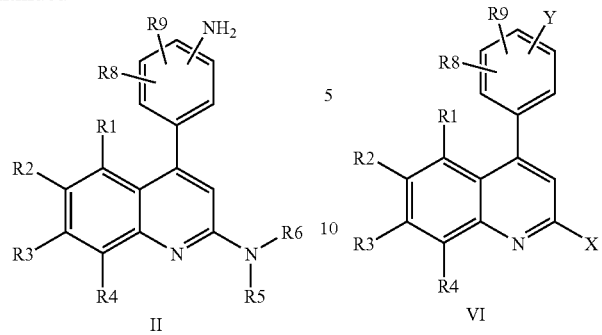

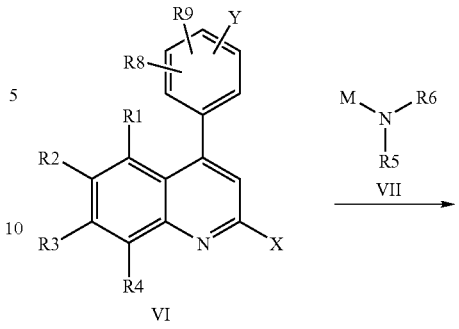

where the substituents R1, R2, R3, R4, R5, R6, R8, R9 are defined above. The reduction can take place by processes known in the art, for example by catalytic hydrogenation or with an inorganic reducing agent such as, for example, with iron powder and hydrochloric acid in glacial acetic acid.

Compounds of the formula IVa in which R5 and R6 are hydrogen can be prepared for example by reacting compounds of the formula V in an alkaline condensation with acetonitrile (see for example, I. A. Nicolls et al., Life Sciences 53, 343-347 (1993) to give compounds of the formula IVb,

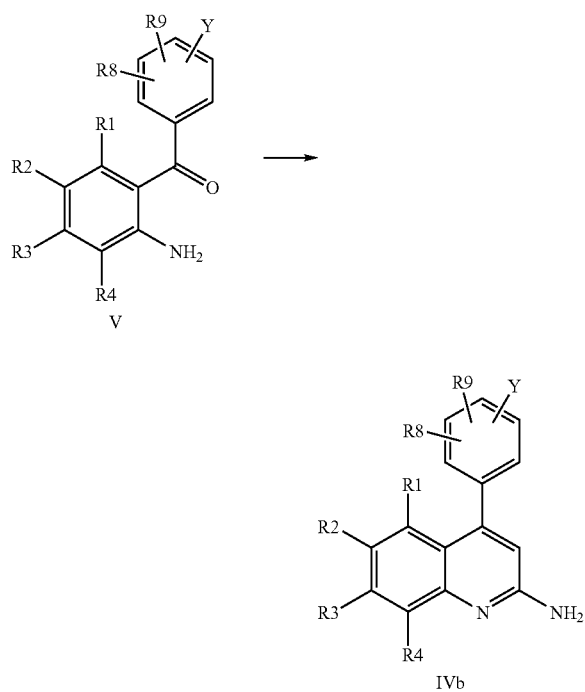

where R1, R2, R3, R4, R8 and R9 have the meaning described above, and Y is hydrogen or $NO_2$. This article is also incorporated herein by reference.

The compounds of the formula IVb in which Y is hydrogen can be converted by nitration into nitro-substituted compounds of the formula IVa in which R5 and R6 are hydrogen.

The compounds of the formula IVa, in which R5 and R6 are not both hydrogen, are obtained, for example, by nucleophilic exchange reactions of quinoline derivatives of the formula VI with an amine of the formula VII where R1, R2, R3, R4, R5, R6, R8, R9 and Y have the meaning indicated above, but R5 and R6 are not both hydrogen, X represents a leaving group able to undergo nucleophilic substitution, such as, for example, chloride, bromide, tosylate, mesylate, triflate, alkoxy having 1, 2, 3, 4, 5 or 6 C atoms, for example ethoxy, aryloxy, for example phenoxy, or $RS(O)_n$— where n is 0 or 2, and R' is an alkyl radical, preferably having 1, 2, 3 or 4 C atoms, for example, methyl, and M is either hydrogen or a metal, in particular an alkali metal or an alkaline earth metal equivalent, for example lithium, or the compound VII is a Grignard compounds. It is advantageous to employ temperatures of >100° C. with amines, it being possible to recommend the use of an autoclave or a microwave.

Corresponding compounds of the formula IVb in which R5 and R6 are hydrogen can be prepared analogously by reaction with $NH_3$ and under pressure.

The compounds of the formula IVc in which Y is hydrogen can be converted by nitration into nitro-substituted compounds of the formula IVa in which R5 and R6 are not both hydrogen.

Compound VI can be prepared in a manner known to the skilled worker, for example from compounds of the formula VIII for example by the action of an inorganic acid chloride such as phosphorus oxytrichloride, phosphorus trichloride or phosphorus pentachloride for compounds of the formula VI in which X is Cl,

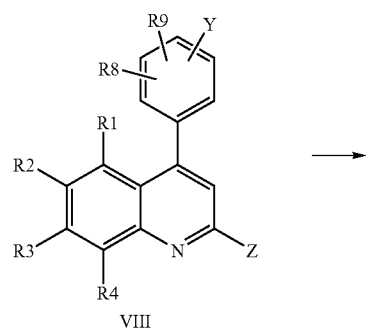

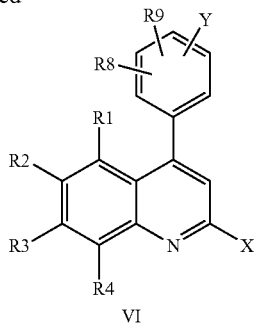

where R1, R2, R3, R4, R8, R9, Y and X have the indicated meaning, and Z is an OH group.

Compounds of the formula I in which R7 is not hydrogen can be prepared by known processes starting from compounds known to the skilled worker, for example compounds such as in Helv. Chim. Act. 1970, 53, 89.

The compounds R10-Hal, R11-Hal, R10-N═C═O, R11-N═C═O and the compounds of the formulae V, VII and VIII can be obtained by purchase or can be prepared by or in analogy to processes described in the literature and known in the art.

The preparation and purification of the compounds of the present invention and/or intermediates thereto can be carried out by process methods such known in the art as extraction, chromatography or crystallization and drying.

Also falling within the scope of the present invention are combinations of an NHE-3 inhibitor of formula I with a carbonic anhydrase inhibitor (e.g. acetazolamide), the latter bringing about a metabolic acidosis and thus itself increasing respiratory activity, so that an enhanced effect and less of the active ingredient of formula I is possible.

As a result of their NHE-3-inhibitory effect, the compounds of the present invention preserve the cellular energy reserves which are rapidly exhausted during toxic and pathogenic events and thus lead to cell damage or cell death. In this connection, the energy-costly ATP-consuming sodium absorption in the proximal tubule temporarily ceases under the influence of NHE-3 inhibitors, and the cell is thus able to survive an acute pathogenic, ischemic or toxic situation. The compounds are therefore suitable for example as pharmaceuticals for the treatment of ischemic noxae, for example of acute renal failure.

The compounds of the present invention are also suitable for the treatment of all chronic renal disorders and types of nephritis which lead, as a consequence of increased protein excretion, to chronic renal failure. Accordingly, the compounds of the formula I are suitable for the manufacture of a medicament for the treatment of late damage from diabetes, of diabetic nephropathy and of chronic renal disorders, in particular of all renal inflammations (nephritides) which are associated with an increased protein/albumin excretion.

It has emerged that the compounds used according to the invention have a mild laxative effect and accordingly can also be used advantageously as laxatives or if there is a risk of constipation.

The compounds of the invention can further be used advantageously for the prevention and therapy of acute and chronic disorders of the intestinal tract which are induced for example by ischemic states in the intestinal region and/or by subsequent reperfusion or by inflammatory states and events. Such complications may arise for example through deficient intestinal peristalsis as are frequently to be observed for example following surgical interventions, associated with constipation or greatly reduced intestinal activity.

It is possible with the compounds of the invention to prevent the formation of gallstones.

The NHE inhibitors of the invention are generally suitable for the treatment of diseases caused by ischemia and by reperfusion.

The compounds of the invention are, as a result of their pharmacological properties, suitable as anti-arrhythmic pharmaceuticals. Owing to their cardioprotective component, the NHE inhibitors are also very suitable for the prophylaxis of infarction and for the treatment of infarction, and for the treatment of angina pectoris, in which case they inhibit or greatly reduce preventively the pathophysiological processes associated with the development of damage induced by ischemia, in particular with the triggering of cardiac arrhythmias induced by ischemia. Because of their protective effects against pathological hypoxic and ischemic situations, the compounds of the formula I used according to the invention can, as a result of inhibition of the cellular $Na^+/H^+$ exchange mechanism, be used as pharmaceuticals for the treatment of all acute or chronic damage induced by ischemia or diseases induced primarily or secondarily thereby.

The present invention also relates to use of the pharmaceutical compounds in surgical interventions. Thus, the compounds of the invention can be used in organ transplantations, in which case the compounds can be used both to protect the organs in the donor before and during removal, to protect removed organs during treatment with or storage thereof in physiological bath fluids, as well as during transfer into the recipient organism pretreated with compounds of formula I.

The compounds are likewise valuable pharmaceuticals with a protective effect for carrying out angioplastic surgical interventions for example on the heart as well as on peripheral organs and vessels.

The compounds of the invention can also be used when performing bypass operations, for example in bypass operations on coronary vessels and in coronary artery bypass graft (CABG).

In accordance with their effect against damage induced by ischemia, the compounds of the invention of the formula I can also be employed in resuscitation following cardiac arrest.

In accordance with their protective effect against damage induced by ischemia, the compounds are also suitable as pharmaceuticals for the treatment of ischemias of the nervous system, especially of the CNS, being suitable for example for the treatment of stroke or of cerebral edema.

Since NHE inhibitors of human tissue and organs protect effectively not only against damage caused by ischemia and reperfusion but also against the cytotoxic effect of pharmaceuticals like those used in particular in cancer therapy and the therapy of autoimmune diseases, combined administration thereof with compounds of the formula I is suitable for reducing or suppressing the cytotoxic effects of a therapy. The reduction in the cytotoxic effects, especially the cardiotoxicity, as a result of co-medication with NHE inhibitors makes it additionally possible to increase the dose of the cytotoxic therapeutic agents and/or to prolong the medication with such pharmaceuticals. The therapeutic benefit of such a cytotoxic therapy can be increased considerably by combination with NHE inhibitors.

The compounds of the formula I are particularly suitable for improving therapy with pharmaceuticals which have an unwanted cardiotoxic component.

In general, the NHE inhibitors described herein can beneficially be combined with other compounds which likewise regulate the intracellular pH, those suitable being inhibitors of the enzyme group of carbonic anhydratases, inhibitors of systems which transport bicarbonate ions, such as the sodium-bicarbonate co-transporter (NBC) or the sodium-dependent chloride-bicarbonate exchanger (NCBE), and with other NHE inhibitors having an inhibitory effect on other NHE subtypes, as combination partners, because they may enhance or modulate the pharmacologically relevant pH-regulating effects of the NHE inhibitors described herein.

In accordance with their protective effect against damage induced by ischemia, the compounds are also suitable as pharmaceuticals for the treatment of ischemias of the nervous system, especially of the central nervous system, being suitable for example for the treatment of stroke or of cerebral edema.

The compounds of the formula I are also suitable for the therapy and prophylaxis of disorders and impairments induced by over-excitability of the central nervous system, in particular for the treatment of epileptiform disorders, centrally induced clonic and tonic spasms, states of mental depression, anxiety disorders and psychoses. The NHE inhibitors of the invention may in this connection be used alone or in combination with other substances having antiepileptic activity or anti-psychotic active ingredients, or carbonic anhydratase inhibitors, for example with acetazolamide, and with further inhibitors of NHE or of the sodium-dependent chloride-bicarbonate exchanger (NCBE).

In addition, the compounds of the invention of the formula I are likewise suitable for the treatment of types of shock such as, for example, of allergic, cardiogenic, hypovolemic and bacterial shock.

The compounds of the formula I can likewise be used for the prevention and treatment of thrombotic disorders because, as NHE inhibitors, they are able to inhibit both platelet aggregation and prevent the excessive release of mediators of inflammation and coagulation, in particular of von Willebrand factor and thrombogenic selectin proteins, which takes place following ischemia and reperfusion. It is thus possible to reduce and eliminate the pathogenic effect of thrombogenic and inflammation-relevant factors. The NHE inhibitors of the present invention can therefore be combined with further anti-coagulant and/or thrombolytic active ingredients such as, for example, recombinant or natural tissue plasminogen activator, streptokinase, urokinase, acetylsalicylic acid, thrombin antagonists, factor Xa antagonists, drugs with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonic anhydratase such as, for example, with acetazolamide is particularly beneficial.

The NHE inhibitors of the invention are additionally notable for a strong inhibitory effect on the proliferation of cells, for example fibroblast cell proliferation and the proliferation of smooth vascular muscle cells. The compounds of the formula I are therefore suitable as valuable therapeutic agents for diseases in which cell proliferation represents a primary or secondary cause, and can therefore be used as anti-atherosclerotic agents against chronic renal failure medications, anti-cancer agents and the like. They can thus be used for the treatment of organ hypertrophies and hyperplasias, for example of the heart and of the prostate. Compounds of the formula I are therefore suitable for the prevention and treatment of heart failure (congestive heart failure=CHF) and for the treatment and prevention of prostate hyperplasia or prostate hypertrophy.

NHE inhibitors are further notable for a retardation or prevention of fibrotic disorders. They are thus suitable as outstanding agents for the treatment of fibroses of the heart, and of pulmonary fibrosis, hepatic fibrosis, renal fibrosis and other fibrotic disorders. Since NHE is significantly elevated in cardiovascular disorders such as hypertension, the compounds of the formula I are suitable for the prevention and treatment of high blood pressure and of cardiovascular disease. They can be used in this connection alone or with a second suitable active agent that is also useful in the treatment of high blood pressure and cardiovascular disorders. Thus, for example, one or more diuretics having a thiazide-like action, loop diuretics, aldosterone and pseudoaldosterone antagonists such as hydrochlorothiazide, indapamide, polythiazide, furosemide, piretanide, torasemide, bumetanide, amiloride, triamterene, spironolactone or eplerone, can be combined with compounds of the formula I. The NHE inhibitors of the present invention can moreover be used in combination with calcium antagonists such as verapamil, diltiazem, amlodipine or nifedipine, and with ACE inhibitors such as, for example, ramipril, enalapril, lisinopril, fosinopril or captopril. Further beneficial combination partners are also β blockers such as metoprolol, albuterol etc., antagonists of the angiotensin receptor and its receptor subtypes such as losartan, irbesartan, valsartan, omapatrilat, gernopatrilat, endothelin antagonists, renin inhibitors, adenosine receptor agonists, inhibitors and activators of potassium channels such as glibenclamide, glimepiride, diazoxide, cromokalim, minoxidil and derivatives thereof, activators of the mitochondrial ATP-sensitive potassium channel (mitoK(ATP) channel), inhibitors of further potassium channels such as of Kv1.5 etc.

As a result of their anti-inflammatory effect, NHE inhibitors of the invention can be used as anti-inflammatory drugs. Mechanistically notable in this connection is the inhibition of the release of mediators of inflammation. The compounds can thus be used alone or in combination with an anti-inflammatory drug for the prevention or treatment of chronic and acute inflammatory disorders. Combination partners which are advantageously used are steroidal and non-steroidal anti-inflammatory drugs.

It has additionally been found that NHE inhibitors show a beneficial effect on serum lipoproteins. They can therefore be used for the prophylaxis and regression of atherosclerotic lesions by eliminating a causal risk factor. These include not only the primary hyperlipidemias, but also certain secondary hyperlipidemias like those occurring for example in association with diabetes. In addition, NHE inhibitors lead to a marked reduction in the infarctions induced by metabolic abnormalities and in particular to a significant reduction in the induced infarct size and its severity. NHE inhibitors of the formula I are therefore advantageously used for the manufacture of a medicament for the treatment of hypercholesterolemia; for the manufacture of a medicament for the prevention of atherogenesis; for the manufacture of a medicament for the prevention and treatment of atherosclerosis, for the manufacture of a medicament for the prevention and treatment of diseases induced by elevated cholesterol levels, for the manufacture of a medicament for the prevention and treatment of diseases induced by endothelial dysfunction, for the manufacture of a medicament for the prevention and treatment of atherosclerosis-induced hypertension, for the manufacture of a medicament for the prevention and treatment of atherosclerosis-induced thromboses, for the manufacture of a medicament for the prevention and treatment of ischemic damage induced by hypercholesterolemia and endothelial dysfunction, and postischemic reperfusion damage, for the manufacture of a medicament for the prevention and treatment of cardiac hypertrophies and cardiomyopathies and of congestive heart failure (CHF), for the manufacture of a medicament for the prevention and treatment of coronary vasospasms and myocardial infarction induced by hypercholesterolemia and endothelial dysfunction, for the manufacture of a medicament for the treatment of said disorders in combinations with hypotensive substances, preferably with angiotension converting enzyme (ACE) inhibitors and angiotensin receptor antagonists. Combination of an NHE inhibitor of the formula I with an active ingredient which lowers the blood lipid level, preferably with an HMG-CoA reductase inhibitor (e.g. lovastatin or pravastatin), where the latter brings about a hypolipidemic effect and thus increases the hypolipidemic properties of the NHE inhibitor of the formula I, represents a favorable combination with enhanced effect and reduced use of active ingredient.

Thus, NHE inhibitors lead to effective protection from endothelial damage of various origins. With this protection of vessels against the syndrome of endothelial dysfunction, NHE inhibitors are valuable pharmaceuticals for the prevention and treatment of coronary vasospasms, peripheral vascular diseases, especially intermittent claudication, atherogenesis and atherosclerosis, left-ventricular hypertrophy and dilated cardiomyopathy, and thrombotic disorders.

NHE inhibitors are additionally suitable for the treatment of non-insulin-dependent diabetes (NIDDM), in which case for example insulin resistance is restrained. It may in this connection be beneficial, for enhancing the anti-diabetic efficacy and quality of the effect of the compounds of the invention, to combine them with a biguanide such as metformin, with an anti-diabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

Besides the acute anti-diabetic effects, NHE inhibitors counteract the development of late complications of diabetes and can therefore be used as pharmaceuticals for the prevention and treatment of late damage from diabetes, such as diabetic nephropathy, diabetic neuropathy, diabetic retinopathy, diabetic cardiomyopathy and other disorders arising as a consequence of diabetes. They can in this connection be advantageously combined with the anti-diabetic pharmaceuticals described above under NIDDM treatment. Combination with a beneficial dosage form of insulin may be particularly important in this connection.

NHE inhibitors show, besides the protective effects against acute ischemic events and the subsequent equally acutely stressing reperfusion events, also direct therapeutically utilizable effects against disorders and impairments of the whole mammalian organism which are associated with the manifestations of the chronically progressive aging process and which are also independent of acute states of defective blood supply and may also occur under normal, non-ischemic conditions. These pathological, age-related manifestations induced over the long aging period, such as disease, invalidity and death, which can now be made amenable to treatment with NHE inhibitors, are disorders and impairments which are essentially caused by age-related changes in vital organs and the function thereof and become increasingly important in the aging organism.

Disorders associated with an age-related functional impairment, and with age-related manifestations of organ degeneration for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors.

An important function and a measure of the maintenance of the reactivity of vessels is the blockade or retardation of the age-related progression of endothelial dysfunction, which can be eliminated highly significantly by NHE inhibitors. NHE inhibitors are thus outstandingly suitable for the treatment and prevention of the age-related progression of endothelial dysfunction, in particular of intermittent claudication. NHE inhibitors are thus outstandingly suitable in addition for the treatment and prevention of heart failure, of congestive heart failure (CHF) and for the treatment and in particular for the prevention of age-related types of cancer.

Combination with hypotensive medicaments such as with ACE inhibitors, angiotensin receptor antagonists, diuretics, $Ca^{2+}$ antagonists etc. or with metabolism-normalizing medicaments such as cholesterol-lowering agents comes into consideration in this connection. The compounds of the formula I are thus suitable for the prevention of age-related tissue changes and for maintaining health and prolonging life while maintaining a high quality of life.

The compounds of the invention are effective inhibitors of the cellular sodium-proton transporter (Na/H exchanger) which in a large number of disorders (essential hypertension, atherosclerosis, diabetes etc.) is also elevated in cells which are easily amenable to measurements, such as, for example, in erythrocytes, platelets or leukocytes. The compounds used according to the invention are therefore suitable as excellent and simple scientific tools, for example in their use as diagnostic aids for diagnosing and distinguishing particular types of hypertension, but also of atherosclerosis, of diabetes and the late complications of diabetes, proliferative disorders etc.

NHE inhibitors are further suitable for the treatment of diseases (human and veterinary) induced by bacteria and by protozoa. In the context of diseases caused by protozoa, particular mention should be made of malarial diseases of humans and coccidiosis of poultry.

The compounds are also suitable as agents for controlling parasites in human and veterinary medicine and in crop protection. Preference is given in this connection to the use as agents against blood-sucking parasites in human and veterinary medicine.

Said compounds are therefore advantageously used alone or in combination with other pharmaceuticals or active ingredients for the manufacture of a medicament for the treatment or prophylaxis of impairments of respiratory drive, of respiratory disorders, sleep-related respiratory disorders, sleep apneas, of snoring, of acute and chronic renal disorders, of acute renal failure and of chronic renal failure, of impairments of bowel function, of high blood pressure, of essential hypertension, of central nervous system disorders, of disorders resulting from CNS over-excitability, epilepsy and centrally induced spasms or of anxiety states, depressions and psychoses, of ischemic states of the peripheral or central nervous system or of stroke, of acute and chronic damage and disorders of peripheral organs or limbs caused by ischemic or reperfusion events, of atherosclerosis, of impairments of lipid metabolism, of thromboses, of impairments of biliary function, of infestation by ectoparasites, of disorders resulting from endothelial dysfunction, of protozoal diseases, of malaria, for the preservation and storage of transplants for surgical procedures, for use in surgical operations and organ transplantations or for the treatment of states of shock or of diabetes and late damage from diabetes or of diseases in which cell proliferation represents a primary or secondary cause, and for maintaining health and prolonging life.

The invention further relates to the use of the compounds of the formula I and the pharmaceutically acceptable salts thereof for use as medicament.

The invention also relates to medicines/pharmaceutical preparations for human, veterinary or phytoprotective use comprising an effective amount of a compound of the formula I and/or of a pharmaceutically acceptable salt thereof, as well as pharmaceutical preparations for human, veterinary or phytoprotective use comprising an effective amount of a compound of the formula I and/or of a pharmaceutically acceptable salt thereof alone or in combination with one or more other pharmacological active ingredients or pharmaceuticals.

Pharmaceuticals which comprise a compound of the formula I or the pharmaceutically acceptable salts thereof can be administered for example orally, parenterally, intramuscularly, intravenously, rectally, nasally, by inhalation, subcutaneously or by a suitable transcutaneous dosage form, the preferred administration depending on the respective manifestation of the disorder. The compounds of the formula I can moreover be used alone or together with pharmaceutical excipients, specifically both in veterinary and in human medicine and in crop protection. The pharmaceuticals comprise active ingredients of the formula I and/or pharmaceutically acceptable salts thereof generally in an amount of from 0.01 mg to 1 g per dose unit.

Excipients that are useful in the preparation of the desired pharmaceutical formulation. Besides solvents, gel formers, suppository bases, tablet excipients and other active ingredient carriers it is possible to use for example antioxidants, dispersants, emulsifiers, antifoams, masking flavors, preservatives, solubilizers or colorants.

For oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry and as wet granules. Examples of suitable oily carriers or solvents are vegetable or animal oils, such as sunflower oil or fish liver oil.

For subcutaneous, percutaneous or intravenous administration, the active compounds used are converted, if desired with the substances usual for this purpose, such as solubilizers, emulsifiers or further excipients, into solution, suspension or emulsion. Examples of suitable solubilizers are: water, physiological saline or alcohols, e.g. ethanol, propanol, glycerol, as well as sugar solutions such as glucose or mannitol solutions, or also a mixture of the various solvents mentioned. Suitable as pharmaceutical formulation for administration in the form of aerosols or sprays are for example solutions, suspensions or emulsions of the active ingredient of the formula I in a pharmaceutically acceptable solvent such as, in particular, ethanol or water, or a mixture of such solvents. The formulation may, if required, also comprise other pharmaceutical excipients such as surfactants, emulsifiers and stabilizers, and a propellant gas. Such a preparation normally comprises the active ingredient in a concentration of about 0.1 to 10, in particular of about 0.3 to 3% by weight.

The dosage of the active ingredient of the formula I to be administered and the frequency of administration depend on the potency and duration of action of the compounds used; additionally also on the nature and severity of the disease to be treated and on the gender, age, weight and individual response of the mammal to be treated.

On average, the daily dose of a compound of the formula I for a patient weighing about 75 kg is at least 0.001 mg/kg, preferably 0.1 mg/kg, to a maximum of 30 mg/kg, preferably 1 mg/kg, of body weight. In acute situations, for example immediately after suffering apneic states at high altitude, higher doses may also be necessary. Up to 300 mg/kg per day may be necessary in particular on i.v. administration, for example for an infarct patient in intensive care. The daily dose can be divided into one or more, for example up to 4, single doses.

DESCRIPTIONS OF EXPERIMENTS AND EXAMPLES

List of Abbreviations Used m.p. melting point
min. minutes
MPRC Cartridge L-026-30; SI60 40-63 µm; Super Vario Flash; max. press. 3 bar Götec-Labortechnik GmbH
MPLC medium pressure liquid chromatography Example 1

2-Amino-4-(4-aminophenyl)-6-chloro-3,4-dihydro-quinoline hydrochloride

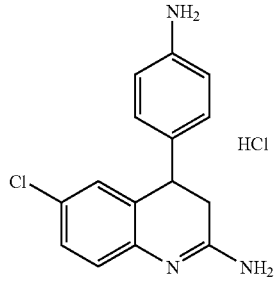

a) 2-Amino-6-chloro-4-phenylquinoline

A suspension of 1.4 g of powdered KOH in 25 ml of anhydrous acetonitrile stirred under an argon atmosphere was heated to boiling under reflux conditions for 30 minutes and then a solution of 1.15 g of 2-amino-5-chlorobenzophenone in 5 ml of anhydrous acetonitrile was added. The mixture was boiled with a reflux condenser for 12 hours. Cooling was followed by pouring into ice, extraction with ethyl acetate, washing with water and removal of the solvent by distillation.
m.p.: 123-125° C.

b) 2-Acetylamino-6-chloro-4-phenylquinoline

A mixture of 0.1 g of 2-amino-6-chloro-4-phenylquinoline and 8 ml of acetic anhydride was stirred at 70° C. for 1 hour, the solvent was removed by distillation, the solid residue was stirred with water, and the crystalline substance was filtered off.
m.p.: 178-182° C.

c) 2-Acetylamino-6-chloro-4-(4-nitrophenyl)quinoline 200 mg of 2-acetylamino-6-chloro-4-phenylquinoline were introduced in portions into 4 ml of 100% strength $HNO_3$ at 0° C. and stirred at 0° C. to 5° C. for 30 min, and the reaction mixture was poured into ice-water. Neutralization with 2N NaOH was followed by extraction with ethyl acetate and removal of the solvent by distillation. The solid residue was boiled several times with diisopropyl ether, and the solvent of the filtrate was evaporated until the substance separated out as crystals.

m.p.: above 180° C. with decomposition.

d) 2-Amino-6-chloro-4-(4-aminophenyl)quinoline 1.8 ml of concentrated hydrochloric acid were added dropwise to a suspension of 0.59 g of 2-acetylamino-6-chloro-4-(4-nitrophenyl)quinoline and 0.29 g of iron powder, and then the reaction mixture was heated under reflux for 4 hours and filtered while hot. The solvent was removed by distillation, an MPLC was carried out on an MPRC cartridge with a mixture of 10 parts by volume of dichloromethane and 1 part by volume of methanol, and the substance was obtained as a yellow viscous oil.

e) 2-Amino-4-(4-aminophenyl)-6-chloro-3,4-dihydroquinoline 6.76 g of sodium amalgam were added over the course of one hour to a solution of 255 mg of 2-amino-6-chloro-4-(4-aminophenyl)quinoline in 3.4 ml of water and 22 ml of ethanol while stirring. The mixture was stirred overnight and decanted off from the Hg precipitate, and the solvent was removed by distillation under reduced pressure. After carrying out an MPLC column chromatography in a mixture of 10 parts by volume of ethyl acetate, 5 parts by volume of methanol, 5 parts by volume of n-heptane, 5 parts by volume of dichloromethane and 1 part by volume of ammonia (concentrated) and acidification with a little concentrated hydrochloric acid, the solvent was removed by distillation and the residue was induced to crystallize with a little ethyl acetate.

m.p.: above 300° C. with decomposition.

Example 2

4-(4-Aminophenyl)-6-chloro-2-ethylamino-3,4-dihydroquinoline hydrochloride

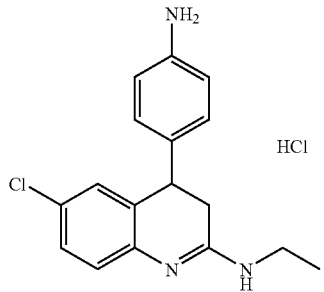

a) 6-Chloro-2-ethylamino 4-(4-nitrophenyl)quinoline 500 mg of 2-acetylamino-6-chloro-4-(4-nitrophenyl)quinoline (compound 1c) were suspended in 10 ml of THF and, under argon, added in portions to 2.9 ml of borane-THF complex. Foaming was followed by formation of a yellow solution. After stirring at room temperature for 12 hours, the solution was mixed with 5 ml of ethanol and 2 ml of concentrated HCl and heated on a water bath, cooled and distilled to remove water. The residue was mixed with water, made alkaline with 2N NaOH, extracted with ethyl acetate and washed with water. The product was purified by MPLC chromatography using an MPRC cartridge with a mixture of 1 part by volume of ethyl acetate, 2 parts by volume of toluene. A yellow solid product was isolated.

m.p.: 145-150° C.

b) 4-(4-Aminophenyl-6-chloro-2-ethylamino)quinoline 254 mg of 6-chloro-2-ethylamino-4-(4-nitrophenyl)quinoline were suspended in 1.6 ml of diglyme, and 9 mg of iron phthalocyanine and 97 mg of 2-bromoethanol were added. The mixture was stirred at room temperature for 3 minutes and then 3.1 ml of NaBH$_4$ solution (0.5M in diglyme) were injected. An exothermic reaction took place and was kept at room temperature with a water bath. The greenish black mixture was stirred at room temperature for 4 hours. The mixture was mixed with water and extracted with ethyl acetate. The product was purified by MPLC chromatography using an MPRC cartridge with a mixture of 1 part by volume of ethyl acetate and 1 part by volume of toluene. The product was dissolved in a little ethyl acetate, acidified with ethereal HCl, stirred at room temperature and filtered with suction.

m.p.: 308-314° C.

c) 4-(4-Aminophenyl)-6-chloro-2-ethylamino-3,4-dihydroquinoline 148 mg of 4-(4-aminophenyl-6-chloro-2-ethylamino)quinoline were dissolved in 10.3 ml of ethanol and 1.6 ml of water and, over the course of one hour, 3.6 g of sodium/mercury amalgam were added. The mixture was stirred overnight and decanted to remove the Hg precipitate, and the solvent was distilled under reduced pressure. A little concentrated hydrochloric acid was used to acidify, the solvent was removed by distillation, and the residue was induced to crystallize with a little ethyl acetate.

m.p.: above 310° C. with decomposition.

Example 3

4-(4-Aminophenyl)-6-chloro-2-diethylamino-3,4-dihydroquinoline hydrochloride

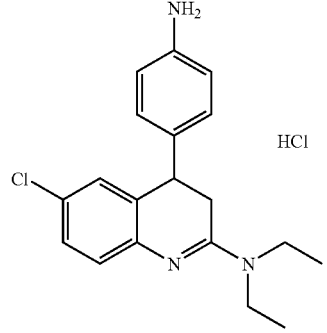

a) 6-Chloro-2-(N-acetyl-N-ethylamino)-4-(4-nitrophenyl)quinoline 600 mg of 6-chloro-2-ethylamino 4-(4-nitrophenyl)quinoline (compound 2a) were added to 0.19 g of acetic anhydride. The mixture was boiled at 70° C. for 4 hours and cooled, and the acetic anhydride was removed by distillation. The residue was mixed with water, extracted with ethyl acetate and washed with water, and the product was obtained as a yellow oil.

b) 6-Chloro-2-diethylamino-4-(4-nitrophenyl)quinoline 570 mg of 6-chloro-2-(N-acetyl-N-ethylamino)-4-(4-nitrophenyl)quinoline were suspended in 11.4 ml of THF and, under argon, added in portions to 3.1 ml of borane-THF complex. The temperature rose to 30° C. After stirring at room temperature for 3 hours, the solvent was removed by distillation and the residue was mixed with 50 ml of ethanol and 20 ml of concentrated HCl and heated on a water bath, cooled and distilled to remove the water. The residue was mixed with water, made alkaline with 2N NaOH, extracted with ethyl acetate and washed with water. The product was purified by MPLC chromatography using an MPRC cartridge with a mixture of 10 parts by volume of ethyl acetate, 5 parts by volume of n-heptane, 5 parts by volume of dichloromethane, 5 parts by volume of methanol and 1 part by volume of concentrated aqueous ammonia solution. A yellow solid product was isolated.

m.p.: 133-138° C.

c) 4-(4-Aminophenyl)-6-chloro-2-diethylaminoquinoline 179 mg of iron powder were added to a solution of 380 mg of 6-chloro-2-diethylamino-4-(4-nitrophenyl)quinoline in 12.7 ml of glacial acetic acid and then 3.0 ml of concentrated hydrochloric acid were added dropwise, and the mixture was boiled at 70° C. for 2 hours. The solvent was removed by distillation, and the residue was mixed with water and made alkaline with 2N NaOH. This aqueous phase was extracted with ethyl acetate. The product is a dark brown viscous oil.

d) 4-(4-Aminophenyl)-6-chloro-2-diethylamino-3,4-dihydroquinoline 5.49 g of sodium/mercury amalgam were added over the course of 5 hours to a solution of 250 mg of 4-(4-aminophenyl)-6-chloro-2-diethylaminoquinoline in 2.5 ml of water and 16 ml of ethanol while stirring. The mixture was stirred overnight and decanted to remove the Hg precipitate, and the solvent was distilled under reduced pressure. The residue was mixed with water and extracted with ethyl acetate. The solid product as pale residue was dissolved in a little ethyl acetate, acidified with ethereal HCl, stirred at room temperature and filtered with suction.

m.p.: 128-134° C.

Example 4

N-(2-Dimethylaminoethyl)-N'-4-[(6-chloro-3,4-dihydro-2-diethyl-aminoquinolin-4-yl)phenyl]urea hydrochloride

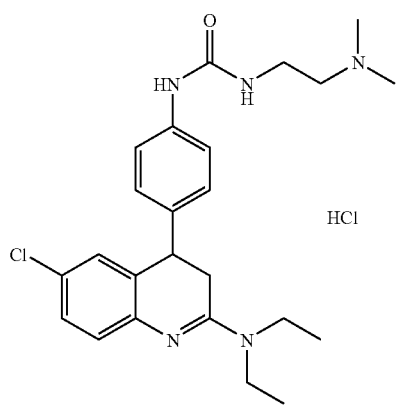

a) O-(2-Nitrophenyl)-N'-4-[(6-chloro-3,4-dihydro-2-diethylaminoquinolin-4-yl)phenyl]-carbamate 62 mg of 4-(4-aminophenyl)-6-chloro-2-diethylamino-3,4-dihydroquinoline (example 3) were dissolved in 5 ml of dichloromethane, and 46 mg of 4-nitrophenyl chloroformate were added. A solid precipitates after a short time. After stirring at room temperature for 3 hours, dichloromethane was removed by distillation. The product was isolated as a pale solid.

b) N-(2-Dimethylaminoethyl)-N'-4-[(6-chloro-3,4-dihydro-2-diethylaminoquinolin-4-yl)phenyl]urea 105 mg of O-(2-nitrophenyl)-N'-4-[(6-chloro-3,4-dihydro-2-diethylaminoquinolin-4-yl)phenyl]carbamate were dissolved in 5 ml of THF. Then 21 mg of N,N-dimethylethylenediamine were added dropwise, and the mixture was stirred at room temperature for 4 hours. The solvent was removed by distillation and the residue was extracted with water and ethyl acetate. The product was purified by MPLC chromatography using an MPRC cartridge with a mixture of 10 parts by volume of ethyl acetate, 5 parts by volume of n-heptane, 5 parts by volume of dichloromethane, 5 parts by volume of methanol and 1 part by volume of concentrated aqueous ammonia solution. The resulting product was mixed with water, 2N HCl and 10% HCl, and the clear solution was freeze dried overnight. The product was obtained as a hygroscopic solid product which was dissolved in a little ethyl acetate, acidified with ethereal HCl, stirred at room temperature and filtered with suction.

Rf=0.57 (silica gel, glacial acetic ester/methanol/heptane/dichloromethane/ammonia 10:5:5:5:1)

1H-NMR (DMSO-d6): δ=1.07(t, 2H), 1.17(t, 2H), 2.50(s, 6H), 2.80(d, 2H), 3.13(q, 2H), 3.30(m, 1H), 3.57(m, 1H), 3.70(m, 1H), 3.83(q, 2H), 4.39(m, 1H), 6.66(t, 1H), 6.99(d, 1H), 7.04(d, 2H), 7.43(m, 3H), 7.70(d, 1H), 9.11(s, 1H), MS: m/z=441 (m)+

Pharmacological Data:

Description of Assay: Determination of the NHE-Inhibitory Effect

In this assay, the recovery of the intracellular pH ($pH_i$) after an acidification which occurs even under bicarbonate-free conditions with functional NHE was determined. To this end, the $pH_i$ was determined using the pH-sensitive fluorescent dye BCECF (Calbiochem, the precursor BCECF-AM was employed). The cells were initially loaded with BCECF. The BCECF fluorescence was determined in a ratio fluorescence spectrometer (Photon Technology International, South Brunswick, N.J., USA) with excitation wavelengths of 505 and 440 nm and an emission wavelength of 535 nm and converted into the $pH_i$ using calibration plots. The cells had been incubated in $NH_4Cl$ buffer (pH 7.4) for the BCECF loading ($NH_4Cl$ buffer: 115 mM NaCl, 20 mM $NH_4Cl$, 5 mM KCl, 1 mM $CaCl_2$, 1 mM $MgSO_4$, 20 mM Hepes, 5 mM glucose, 1 mg/ml BSA; a pH of 7.4 was adjusted with 1 M NaOH). The intracellular acidification was induced by adding 975 μl of an $NH_4Cl$-free buffer (see below) to 25 μl aliquots of the cells incubated in $NH_4Cl$ buffer. The subsequent rate of pH recovery was recorded for two minutes with NHE1, five minutes with NHE2 and three minutes with NHE-3. To calculate the inhibitory power of the tested substances, the cells were initially investigated in buffers with which there was complete or absolutely no pH recovery. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM Hepes, 5 mM glucose, a pH of 7.0 was adjusted with 1 M NaOH). To determine the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM Hepes, 5 mM glucose, a pH of 7.0 was adjusted with 1 M NaOH). The substances to be tested were made up in the $Na^+$-containing buffer. The recovery of the intracellular pH at each tested concentration of a substance was expressed as a percentage of the maximum recovery. The $IC_{50}$ of the respective substance for the individual NHE subtypes was calculated from the percentages of pH recovery using the Sigma Plot program.

The inhibitory effect ($IC_{50}$ values) on NHE-3 by various exemplary compounds is detailed in the table below:

| Example | $IC_{50}$ [μM] |
|---|---|
| 1 | 4.39 |
| 2 | 10.87 |
| 3 | 9.19 |
| 4 | 13.85 |

The invention claimed is:

1. A compound of formula I

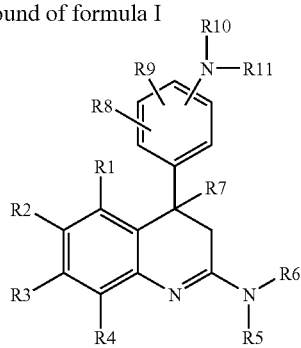

wherein:
R1, R2, R3 and R4 are independently selected from the group consisting of hydrogen, F, Cl, Br, CN, $CF_3$, $CH_3$—$SO_2$, alkyl having 1, 2, 3 or 4 C atoms, $NH_2$, NH—$CH_3$ and $N(CH_3)_2$;
R5 and R6 are independently selected from the group consisting of hydrogen, alkyl having 1, 2, 3, 4, 5 or 6 C atoms, $CF_3$—$CH_2$—, cycloalkyl having 3, 4, 5 or 6 C atoms and cyclopropyl—$CH_2$—,
R7 is a hydrogen
R8 and R9 are independently selected from the group consisting of hydrogen, F, Cl, Br, OH, or alkyl having 1, 2, 3 or 4 C atoms
R10 and R11 are independently of one another R13-($C_mH_{2m}$)—$B_n$, where
m zero, 1, 2, 3 or 4;
n is zero or 1; and
B is —CO—, —CONR14- or —$SO_2$—;
R14 is a hydrogen or an alkyl having 1, 2, 3, 4, 5 or 6 C atoms;
R13 is hydrogen, an alkyl having 1, 2, 3 or 4 C atoms, cycloalkyl having 3, 4, 5 or 6 C atoms, 1-pyrrolidinyl, 1-piperidinyl, 1-(4-methylpiperazinyl), 1-morpholinyl, —COOR15, OR16, NR17R18
R15, R16, R17 and R18 are hydrogen or alkyl having 1, 2, 3, 4, 5 or 6 C atoms;
and the pharmaceutically acceptable salts and trifluoroacetates thereof.

2. The compound of formula I as recited in claim 1, wherein
R1, R2, R3 and R4 are selected from the group consisting of hydrogen, F, Cl, Br, CN, $CF_3$, $CH_3$—$SO_2$,methyl, ethyl, $NH_2$, NH—$CH_3$ and $N(CH_3)_2$;
R5 and R6 are independently selected from the group consisting of hydrogen, methyl, ethyl, isopropyl, $CF_3$—$CH_2$ and cycloalkyl having 3, 4, 5 or 6 C atoms;
R7 is hydrogen;
R8 and R9 are hydrogen, Cl or methyl;
R10 and 11 are R13-($C_mH_{2m}$)—$B_n$, where
m is zero, 1, 2, 3 or 4;
n is zero or 1;
B is —CO—, —CONR14- or —$SO_2$—;
R14 is hydrogen or alkyl having 1, 2, 3, 4, 5 or 6 C atoms;
R13 is selected from the group consisting of hydrogen, methyl, cycloalkyl having 3, 4, 5 or 6 C atoms, 1-pyrrolidinyl, 1-piperidinyl, 1-(4-methylpiperazinyl), —COOR15, OR16 and NR17R18;
R15, R16, R17 and R18 are hydrogen or alkyl having 1, 2, 3, 4, 5 or 6 C atoms;
and the pharmaceutically acceptable salts and trifluoroacetates thereof.

3. The compound of formula I as recited in claim 2, wherein
R1 and R3 are hydrogen;
R2 and R4 are independently of one another hydrogen or Cl;
R5 and R6 are hydrogen, methyl or ethyl;
R7 is hydrogen;
R8 and R9 are hydrogen or Cl;
R10 and 11 are R13-($C_mH_{2m}$)—$B_n$, where
m is zero, 1, 2, 3 or 4;
n is zero or 1;
B is —CONR14-;
R14 is hydrogen or methyl;
R13 is selected from the group consisting of hydrogen, methyl, cycloalkyl having 3, 4, 5 or 6 C atoms, 1-pyrrolidinyl, 1-piperidinyl, 1-(4-methylpiperazinyl), —COOR15, OR16 and NR17R18;
R15, R16, R17 and R18 are hydrogen or alkyl having 1, 2, 3, 4, 5 or 6 C atoms;
or a pharmaceutically acceptable salt or a trifluoroacetate thereof.

4. The compound of the formula I as recited in claim 3, selected from the group consisting of:
2-amino-4-(4-aminophenyl)-6-chloro-3,4-dihydroquinoline,
4-(4-aminophenyl)-6-chloro-2-ethylamino-3,4-dihydroquinoline,
4-(4-aminophenyl)-6-chloro-2-diethylamino-3,4-dihydroquinoline
and
N-(2-dimethylaminoethyl)-N'-4-[(6-chloro-3,4-dihydro-2-diethylaminoquinolin-4-yl)phenyl]urea,
or a pharmaceutically acceptable salt or a trifluoroacetate thereof.

5. A pharmaceutical composition comprising the compounds of formula I as recited in claim 1 and the suitable salts thereof in a pharmaceutically acceptable carrier selected from the group consisting of one or more bulking agents, fillers, solvents, stabilizers, tableting agents, dissolution agents and mixtures thereof.

6. A pharmaceutical composition comprising the compounds of formula I as recited in claim 2 and the suitable salts thereof in a pharmaceutically acceptable carrier selected from the group consisting of one or more bulking agents, fillers, solvents, stabilizers, tableting agents, dissolution agents and mixtures thereof.

7. A pharmaceutical composition comprising the compounds of formula I as recited in claim 4 and the suitable salts thereof in a pharmaceutically acceptable carrier selected from the group consisting of one or more bulking agents, fillers, solvents, stabilizers, tableting agents, dissolution agents and mixtures thereof.

8. A pharmaceutical composition comprising the compounds of formula I as recited in claim 1 and the suitable salts thereof in combination with one or more other pharmaceutical active ingredients in a pharmaceutically acceptable carrier selected from the group consisting of one or more bulking agents, fillers, solvents, stabilizers, tableting agents, dissolution agents and mixtures thereof.

9. A pharmaceutical composition comprising the compounds of formula I as recited in claim 4 and the suitable salts thereof in combination with one or more other pharmaceutical active ingredients in a pharmaceutically acceptable carrier selected from the group consisting of one or more bulking agents, fillers, solvents, stabilizers, tableting agents, dissolution agents and mixtures thereof.

10. The compound of formula I as recited in claim 3 wherein $R_2$ is chloro.

* * * * *